(12) United States Patent
Baird et al.

(10) Patent No.: US 10,739,328 B2
(45) Date of Patent: Aug. 11, 2020

(54) APPARATUS, SYSTEMS, AND METHODS FOR METERING TOTAL WATER CONTENT IN CONCRETE

(71) Applicant: Titan America LLC, Norfolk, VA (US)

(72) Inventors: Kevin Baird, Pembroke Pines, FL (US); Eric Koehler, Miami Beach, FL (US); Cesar Constantino, Roanoke, VA (US); Gary Nininger, Palm City, FL (US); Robert Phelabaum, Melbourne, FL (US); Oscar Bucknor, Jupiter, FL (US)

( * ) Notice: Subject to any disclaimer, the term of this patent is extended or adjusted under 35 U.S.C. 154(b) by 650 days.

(21) Appl. No.: 14/964,370

(22) Filed: Dec. 9, 2015

(65) Prior Publication Data

US 2016/0170419 A1 Jun. 16, 2016

Related U.S. Application Data

(60) Provisional application No. 62/091,197, filed on Dec. 12, 2014.

(51) Int. Cl.
| | | |
|---|---|---|
| *G05D 11/13* | (2006.01) | |
| *G01N 33/38* | (2006.01) | |
| *G01N 33/18* | (2006.01) | |

(52) U.S. Cl.
CPC ........... *G01N 33/383* (2013.01); *G01N 33/18* (2013.01)

(58) Field of Classification Search
CPC ............ G01N 33/383; B01F 15/00025; B08B 9/0813; B08B 9/093
See application file for complete search history.

(56) References Cited

U.S. PATENT DOCUMENTS

| | | | | |
|---|---|---|---|---|
| 1,922,700 A | * | 8/1933 | Knowles | ............... B28C 5/4231 366/34 |
| 3,336,011 A | * | 8/1967 | Futty | ..................... B28C 7/0413 222/223 |
| 3,767,170 A | * | 10/1973 | Morgenstern | ......... B28C 7/0486 366/3 |
| 4,008,093 A | | 2/1977 | Kao | |
| 4,318,177 A | | 3/1982 | Raap | |
| 4,356,723 A | | 11/1982 | Fay | |
| 5,713,663 A | | 2/1998 | Zandberg | |
| 5,752,768 A | | 5/1998 | Assh | |
| 5,895,116 A | * | 4/1999 | Kreinheder | ............... B28C 7/04 366/142 |
| 5,975,133 A | * | 11/1999 | Nalewajski | ............. E03B 11/02 137/587 |
| 6,042,259 A | * | 3/2000 | Hines | ..................... B28C 7/024 366/17 |

(Continued)

*Primary Examiner* — Tony G Soohoo
*Assistant Examiner* — Elizabeth Insler
(74) *Attorney, Agent, or Firm* — Williams Mullen; F. Michael Sajovec (57) ABSTRACT

An apparatus, system, and method for metering the total water added to a concrete load contained in a concrete truck mixing drum. The apparatus includes a coupling for connecting an external water supply, at least two check valves to enable water to be added from either the external water supply or a water tank onboard the truck, and a meter for recording water added to the concrete drum. Separate hoses may be provided for adding water to the drum and for supplying water for use outside the concrete drum.

12 Claims, 6 Drawing Sheets

(56) References Cited

U.S. PATENT DOCUMENTS

| | | |
|---|---|---|
| 6,484,079 B2 | 11/2002 | Buckelew |
| 6,611,755 B1 | 8/2003 | Coffee et al. |
| 6,768,994 B1 | 7/2004 | Howard et al. |
| 6,862,521 B1 | 3/2005 | Fox |
| 6,892,131 B2 | 5/2005 | Coffee et al. |
| 7,489,993 B2 | 2/2009 | Coffee et al. |
| 7,530,728 B2 | 5/2009 | Rosean |
| 7,780,335 B2 | 8/2010 | Rosean |
| 8,020,431 B2 | 9/2011 | Verifi |
| 8,118,473 B2 | 2/2012 | Verifi |
| 8,311,678 B2 | 11/2012 | Verifi |
| 8,616,758 B2 * | 12/2013 | Takahashi ............ B28C 5/4213 366/61 |
| 8,746,954 B2 * | 6/2014 | Cooley .................. B28C 5/422 366/143 |
| 8,911,138 B2 * | 12/2014 | Cook ..................... B28C 5/422 366/19 |
| 8,989,905 B2 * | 3/2015 | Sostaric ........... B01F 15/00207 361/1 |
| 2002/0015354 A1 | 2/2002 | Buckelew |
| 2005/0159843 A1 * | 7/2005 | Oberg ................ B01F 15/0479 700/265 |
| 2010/0246312 A1 * | 9/2010 | Welker ................ B01F 3/04439 366/4 |

* cited by examiner

PRIOR ART

FIG. 5

PRIOR ART

APPARATUS, SYSTEMS, AND METHODS FOR METERING TOTAL WATER CONTENT IN CONCRETE

CROSS REFERENCE TO RELATED APPLICATIONS

This application claims the benefit of U.S. Provisional Application No. 62/091,197, filed Dec. 12, 2014.

STATEMENT REGARDING GOVERNMENT SUPPORT

None.

FIELD

The present disclosure relates to measuring the amount of water added to a concrete load, such as water added to a concrete load contained in a concrete truck mixer drum.

BACKGROUND

Concrete is a composite material manufactured by mixing together portland cement, fine aggregate (sand), coarse aggregate (gravel or crush rock), and water. Other potential ingredients include supplementary cementitious materials—such as fly ash, slag cement, and silica fume—and chemical admixtures—such as water reducers, set accelerators, set retarders, and air entraining agents.

The addition of water to portland cement results in a series of chemical reactions, known as hydration, ultimately resulting in hardened cement paste that binds together coarse and fine aggregate to form hardened concrete. Some water is needed for hydration; however, too much water damages concrete hardened properties such as strength and durability. Increasing the water content also improves the workability and flowability of concrete, often measured with the slump test. Concrete is designed with specific water content to achieve the desired workability and hardened properties needed for the application. If too little water is added, the concrete is stiff and difficult to pour and finish. If too much water is added, the strength and durability are poor.

For ready mix concrete, the individual ingredients are batched in a central plant and transported by truck to the jobsite. The ingredients may be first mixed in a stationary mixer at the plant and then added to the truck mixing drum (or "concrete drum") or they may be added directly to the truck mixing drum where all mixing takes place.

Water is added to concrete from multiple sources. During batching, water is introduced directly into the concrete drum along with the other dry ingredients. In addition, aggregates contain some moisture, which must be accounted for when determining total water content. It is common to batch less water than the design, such that water can be added later if the slump is less than desired. Once the truck is loaded, it typically moves to the "slump rack" (also known as the "wash rack") in the plant yard. Here, the driver washes off any dust that collects on the outside of the truck during batching. He washes down into the concrete drum any material that collects on the top of the inside of the concrete drum and on the hopper for loading the truck. In addition, the driver checks the slump and may add water if the slump is less than target. Unexpected variation in batching or material quality may result in the slump being less than desired and necessitate a slump adjustment at the slump rack. Once the truck leaves the plant, the driver may add more water during transit or on the jobsite before or after pouring to increase the slump. This may be necessary because slump typically decreases over time.

It is essential that all water be measured and compared to the design amount. Water in the form of aggregate moisture is measured with aggregate moisture meters (e.g. microwave or resistivity meters) or by collecting a sample, drying the sample to remove all water, and recording the mass of water evaporated. Water added during batching is measured by weight or with a flow meter. Trucks are equipped with water tanks for adding water to the concrete drum in transit or at the jobsite. The amount added may be measured with a flow meter on the truck or a graduated sight tube on the water tank.

Any water added in the plant after batching is difficult to measure. Truck drivers typically use a hose from the plant, which is external to the truck, to wash the truck and add water to the concrete drum. This hose is typically not metered. Even if it were metered, the hose is common for all trucks, so it is difficult to track which truck the water went to and whether the water was added to the concrete drum or used to wash the exterior of the truck.

The water added from the truck tank may also be used for purposes other than adjusting the concrete. For example, some water is used to clean the chutes and tools.

It is also important to know when water was added, relative to the delivery cycle. For example, if water is added after pouring has started, the purchaser of the concrete is typically responsible for any negative consequences of this water addition. However, the ready mix concrete supplier is typically responsible for the consequences of any water added prior to delivery on the jobsite.

Therefore, what is needed is an apparatus, system, and method to measure all water added to the concrete drum and to exclude any water coming from the truck tank but not added to the concrete drum. It is also important to achieve this goal without increasing the amount of time to deliver a load of concrete.

BRIEF SUMMARY

This disclosure relates to devices, systems, and methods for measuring the amount of water added to a concrete load, and in particular a concrete load as it transitions from a manufacturing location to an ultimate jobsite. For example, the devices, systems, and methods described herein may be used to measure the total water added to a concrete load contained in a concrete truck mixer drum over time.

In the present approach to measuring and controlling water, the water added during batching is measured and recorded. Water added to the truck after batching but while still at the plant is not metered or recorded. Water from the truck tank may be recorded at the jobsite based on a flow meter on the truck or a graduated sight tube on the truck water tank; however, the present approach does not facilitate distinguishing the portion of the water from the truck tank that goes into the mixing drum and the portion used external to the mixing drum, such as for washing tools and the chutes.

Therefore, it is an object of this disclosure to describe apparatus, systems, and methods for measuring the total water added to the truck mixing drum while excluding any water used during delivery but not added to the mixing drum. It is a further objective of the apparatus, systems, and methods described in this disclosure to identify the stage of delivery when the water is added and to compare the total added at each stage to the amount allowed by the concrete mix design.

The apparatus, systems, and methods described herein enable water to be added at the plant without slowing down the driver from leaving the plant. It is important for the truck to leave the plant as soon as possible to maximize the number of loads a truck can transport in one day. The driver can use one hose to add water through the system while simultaneously using separate hoses to fill the truck water tank and wash the exterior of the truck.

The apparatus, systems, and methods described herein help ensure the total amount of water allowed by the concrete mix design is not exceeded, thus ensuring the hardened concrete meets design requirements for strength and durability.

DESCRIPTION

The following description is of the best currently contemplated mode of carrying out exemplary embodiments of the disclosed apparatus, systems, and methods. The description is not to be taken in a limiting sense, and is made merely for the purpose of illustrating the general principles of the disclosure.

Concrete is normally produced according to a mix design. The ingredients and quantities of materials are typically selected to achieve the desired plastic, setting, and hardened concrete properties for the mix design.

Requirements for plastic properties, which relate to the time before concrete begins to harden, include slump, air content, bleeding, and segregation. Concrete slump is a measure of the workability, or ease of pouring and placement. In the slump test, concrete is placed in a frustum of a cone, the cone is removed, and the distance the concrete falls or "slumps" is measured. Higher slumps are associated with more flowable concrete. The slump test is standardized as ASTM C143. Concrete may contain entrained air, which is intentionally added to provide resistance to freezing and thawing. Bleeding involves the movement of water to the surface of the concrete. Segregation involves the settling of heavier particles to the bottom of the concrete, resulting in concrete that is not homogeneous in composition and performance.

The setting time is defined as the time from first mixing until the concrete begins to solidify. Hardened properties include compressive strength, flexural strength, modulus of elasticity, shrinkage, and permeability.

All of these properties are closely related to the amount of water added to the mixture, and more particularly to the ratio of the mass of water to mass of cementitious materials. Cementitious materials are added once at the concrete plant, but water can be added throughout the delivery cycle. Therefore, this disclosure describes a device, system, and method to more precisely meter and control the amount of water added to a concrete mixture during production to ensure concrete exhibits desired properties.

The slump of concrete typically decreases with time, due to the hydration of the cementitious materials. Increasing the water content results in increased slump. Therefore, even if the correct amount of water is added during batching at the plant, it may be necessary to add more water over time. The delivery time can be unpredictable due to factors such as traffic and jobsite delays. Higher temperatures also increase slump loss with time, requiring more water to be added. The mix design typically includes a portion of water that can be added on site. However, it is important this amount not be exceeded. Because it is easier to work with concrete at higher slump, it is tempting for jobsite personnel to add water to increase slump and make pouring easier and faster.

Concrete is transported from a concrete plant to the jobsite in a concrete truck. The truck has a mixing drum, which is typically rotated by a hydraulic motor at low agitating speed (e.g. 1-6 rpm) and faster mixing speed (e.g. 12-18 rpm). The concrete drum is operated in reverse to remove concrete from the drum and convey the concrete down a chute. The concrete drum has a series of mixing fins to mix concrete and remove concrete from the drum.

The concrete truck includes an onboard water tank for 1) adding water to the concrete drum to adjust the concrete and/or wash the drum's interior, 2) washing the truck's exterior, and 3) washing tools, chutes and other equipment not on the truck.

Figure 1:
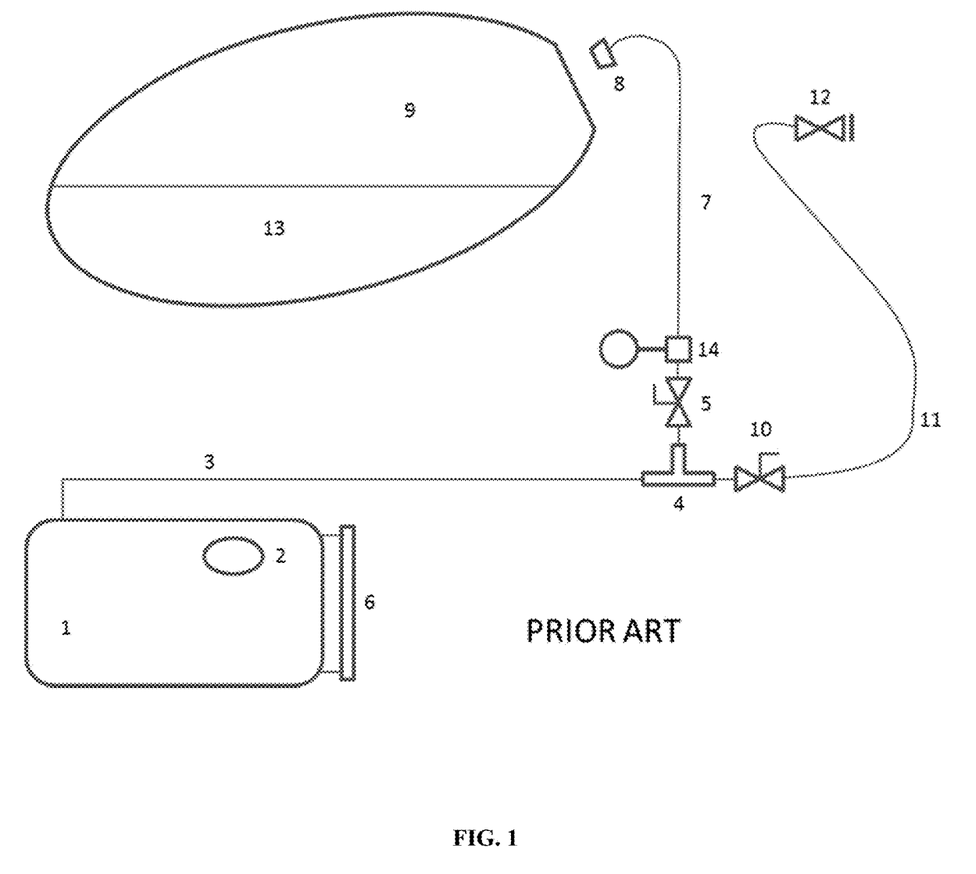
FIG. 1 is a schematic diagram of a typical water delivery apparatus on a concrete truck.

FIG. 1 shows the components of a typical water delivery apparatus on a concrete truck with concrete drum 9 for mixing and transporting concrete 13. The water tank 1 with filling port 2 is mounted to the truck and is connected to the rest of the water delivery system by a hose 3. A tee fitting 4 is provided to allow water to be diverted to a separate hose 11 and nozzle 12 for washing the truck. A first ball valve 10 is provided to stop the flow of water in the event the nozzle fails. A second ball valve 5 is provided to control the flow of water to the drum via hose 7. This valve is normally closed and is opened to add water to the drum. A nozzle 8 controls the trajectory of water added to the drum.

The amount of water added to the drum can be recorded with the water meter 14 or sight tube 6. However, note that some water recorded on the sight tube 6 may be used via the separate hose 11 and nozzle 12 for washing the exterior of the truck. In addition, the driver needs to clean the hopper to the drum and top of the drum itself. Because water is directed into the drum through nozzle 8, it is necessary to use hose 11 and 12 for this task. As a result, this amount of water would not be recorded through meter 14 even though it is added to the drum, resulting in inaccurate measurement of the amount of water added to the concrete.

The water tank is typically pressurized by air, which forces water through the hoses when one or more ball valves are open. The pressure is not applied when the tank is being filled through port 2. Therefore, water cannot be added to the drum from the tank when the tank is being filled.

Figure 2:
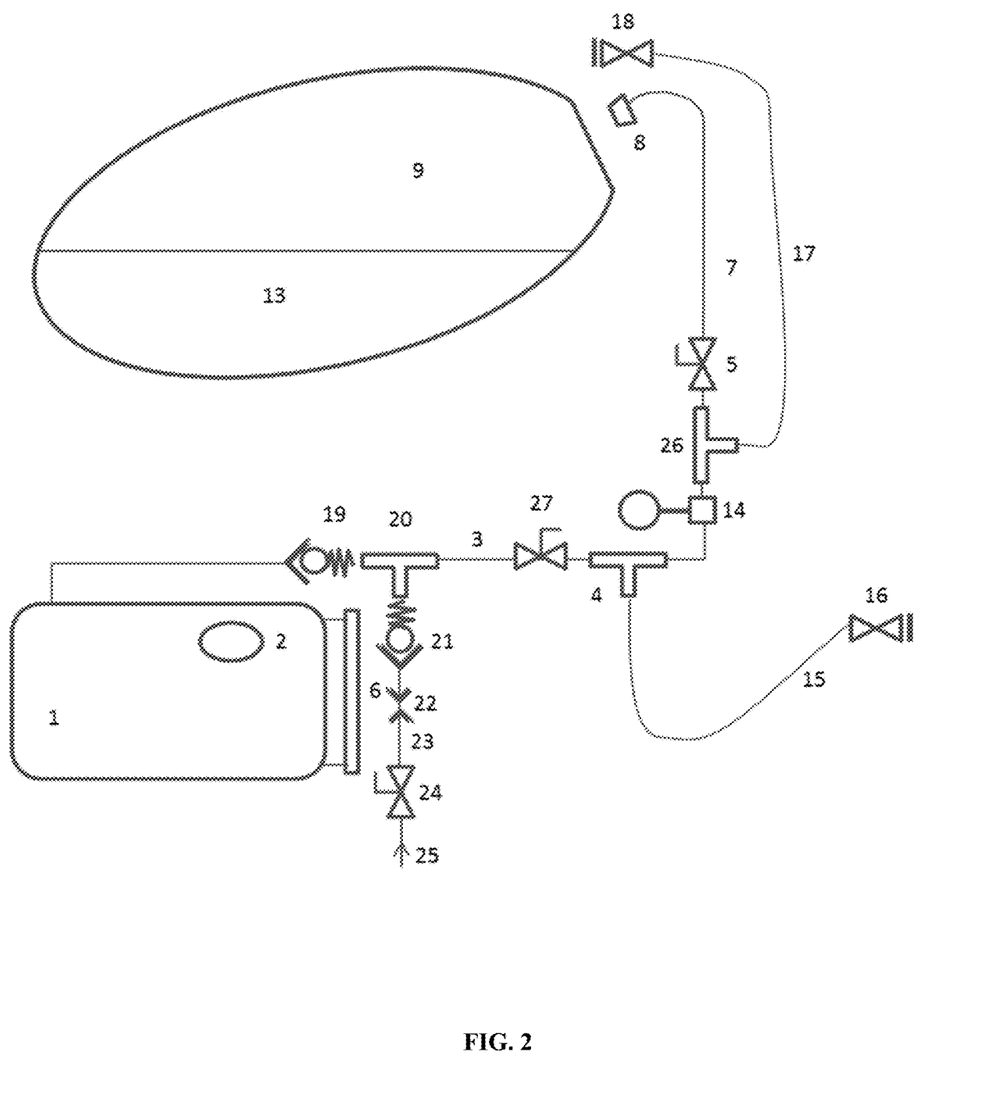
FIG. 2 is a schematic diagram of an embodiment of an apparatus for measuring and controlling total water added to concrete according to the present disclosure.

FIG. 2 shows an apparatus for metering total water added to the concrete according to one embodiment. An external water source 25 is connected by a hose 23 at a coupling 22. A ball valve 24 can be opened to allow water to flow to the truck water system. A first check valve 21 is provided downstream of the coupling and upstream of a first joint 20 for preventing water from flowing toward the coupling but allowing water to flow from the external source. A second check valve 19 is provided downstream of the water tank and upstream of a first joint 20, for preventing water from flowing toward the water tank but allowing water to flow when provided from the water tank. A ball valve 27 controls water flowing to the drum 9 and hose 15 and nozzle 16, which are used to wash the exterior of the truck, and hose 17 and nozzle 18 used to wash the interior of the drum. The joint 4 is provided upstream of the meter 14 so that water used to wash the exterior of the truck with hose 15 and nozzle 16 is not recorded by meter 14. The joint 26, however, is provided downstream of the meter so that water used to wash the interior of the concrete drum 9 with hose 17 and nozzle 18 is recorded by meter 14. As with FIG. 1, the ball valve 5 in FIG. 2 is used to control water flowing to the drum.

Figure 3:
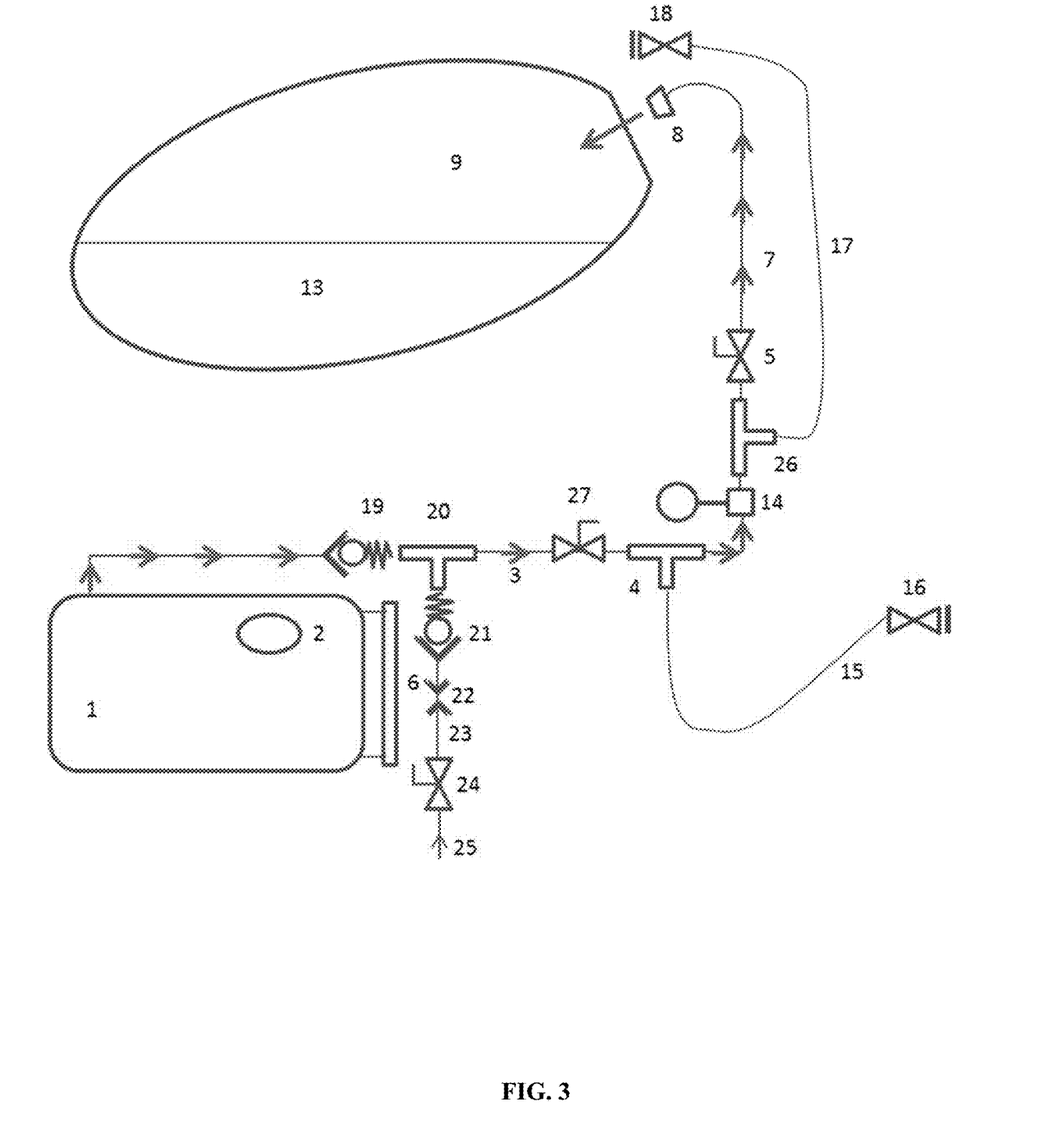
FIG. 3 is a schematic diagram of the present disclosure, indicating fluid flow to the concrete drum when water is added from the tank.

The operation of the check valves can be further described based on FIG. 3, which illustrates the flow of water when supplied to the drum 9 from the water tank 1. The water flows through check valve 19 and is prevented from flowing out check valve 21. To achieve this flow, the driver would open ball valve 27 and ball valve 5 while keeping ball valve 24 closed.

Figure 4:
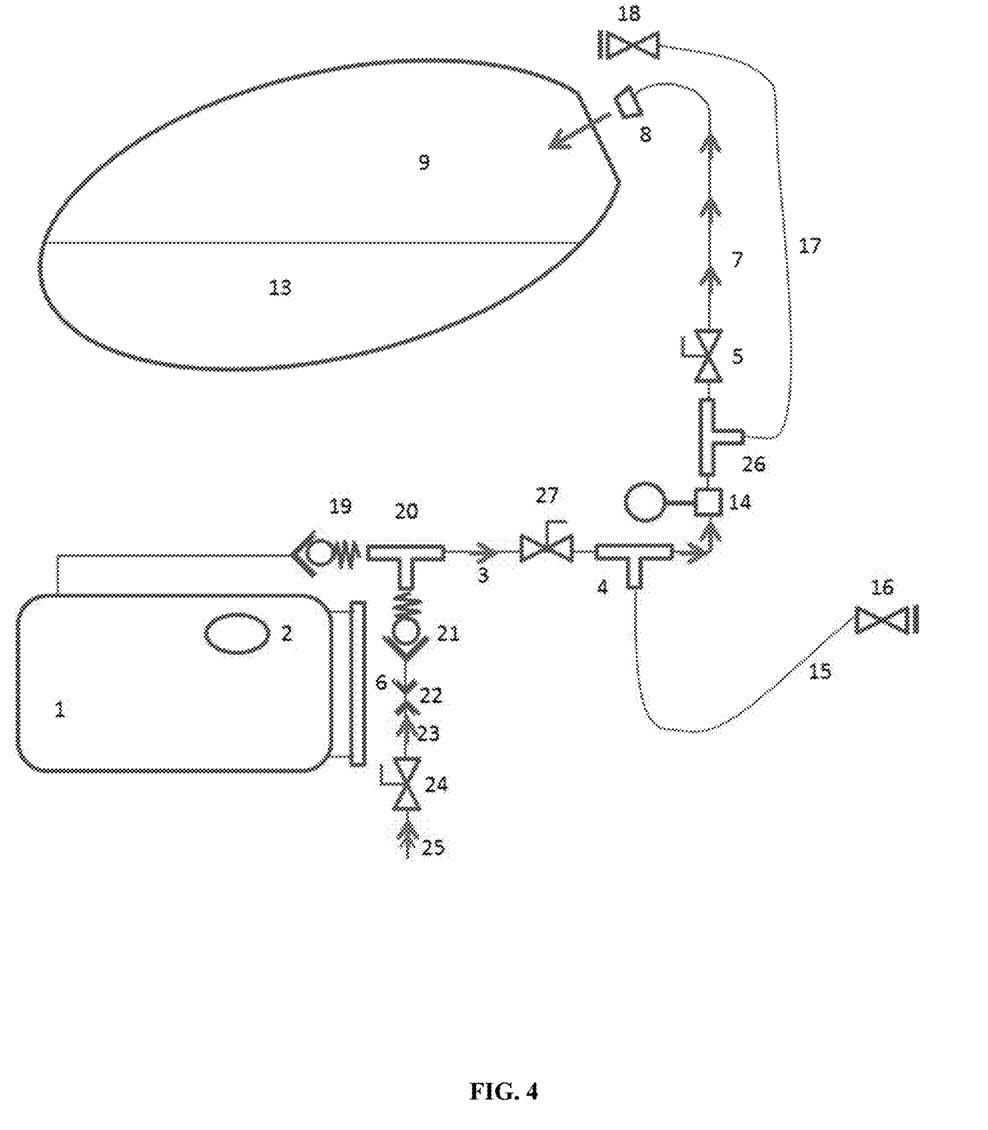
FIG. 4 is a schematic diagram of the present disclosure, indicating fluid flow to the concrete drum when water is added from the external source.

FIG. 4 illustrates the flow of water when supplied to the drum 9 from the external source. The water flows through check valve 21 and is prevented from flowing out check valve 19. To achieve this flow, the driver would connect external source 25, open ball valve 27 and ball valve 25, and have the tank in a depressurized state.

Figure 5:
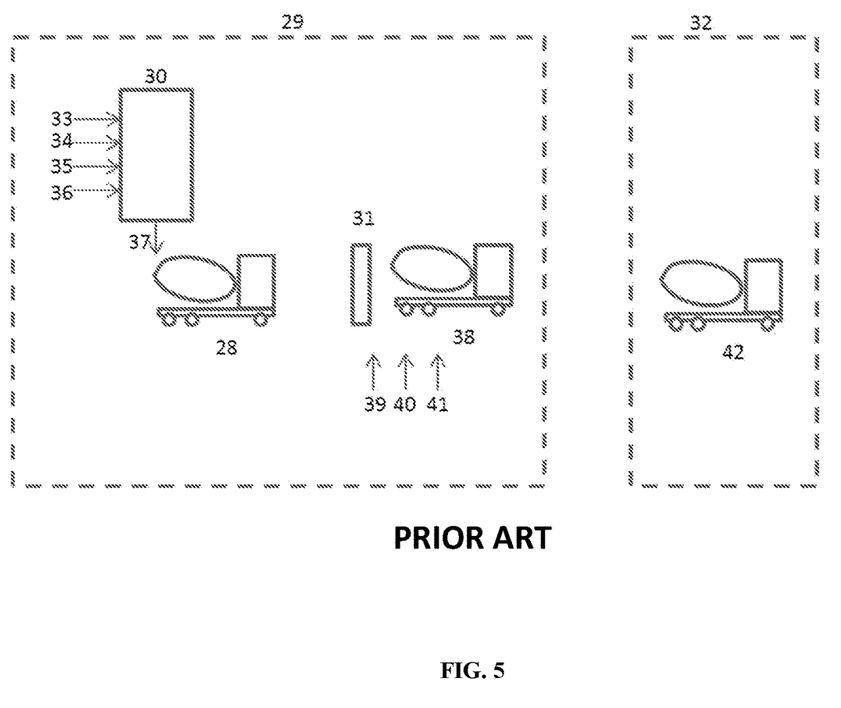
FIG. 5 is a diagram of a ready mix concrete plant and jobsite.

FIG. 5 shows the physical locations of a concrete truck during a delivery cycle. The truck 28 is first at the batch plant 30, where the proper amount of ingredients are batched from a cement source 33, fine aggregate source 34, coarse aggregate source 35 and water source 36. The ingredients are added to the truck 28 via a hopper 37 on the truck.

The truck 38 then moves to the slump/wash rack 31 while still in the plant yard 29. There are three sources of water provided, including first water supply 39 for filling the water tank on the truck, a second water supply 40 for washing the exterior of the truck, and a third water supply 41 for adding water to the drum. The said first water supply may also be provided at the batch plant.

The truck 42 then moves to the jobsite 32 where the concrete is poured.

A system for metering water to a concrete truck may include an apparatus such as described above and one or more integrated concrete operations. A concrete operation typically includes a computer system running a dispatch software program, which is typically located centrally for a company or region. A plant may have batch software to control the loading of ingredients into the truck, or access to a distributed network providing batch software. For instance, a plant, or another building in the system, may operate a computer-implemented batching system. The trucks may be equipped with a tracking system, which may be linked to the dispatch software via a centralized truck tracking software. Typical tracking systems include an on-truck computer processor with a cellular modem, driver user interface, GPS sensor, and other sensors for monitoring truck activity. For instance, some tracking systems include a drum rotation sensor capable of monitoring the speed and direction of the drum, a hydraulic pressure sensor to determine the pressure required to operate the drum (which can be related to concrete slump), and a water meter for recording the amount of water flowing from the water tank. The sensor data on the truck tracking system can be used to determine the stages of the delivery process. For instance, the GPS sensor can indicate when the truck leaves the plant site. The time when the truck begins pouring can be detected when the GPS sensor indicates the truck is on the jobsite and the drum rotation sensor indicates the drum is rotating in the reverse, discharge direction. Data is sent to a central tracking database, which may interface to dispatch software, billing software, or enterprise resource planning software. Dispatchers use the data to track the location and status of trucks and to schedule trucks for pending orders.

Figure 6:
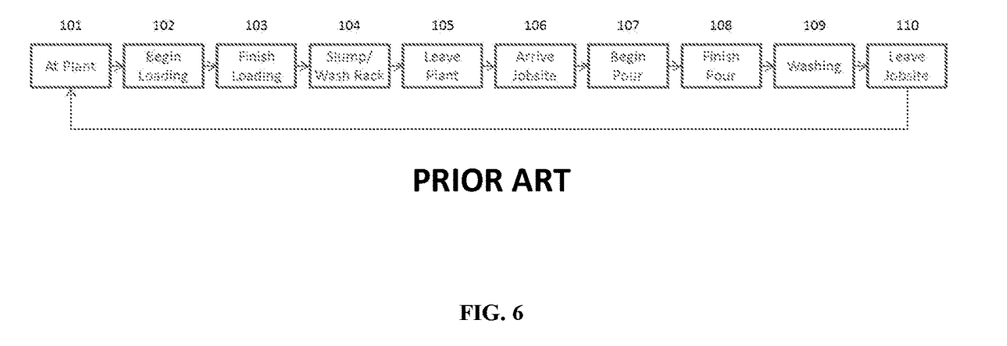
FIG. 6 is a flow chart of the typical delivery process for ready mix concrete.

The typical delivery process is shown in the flow chart in FIG. 6. The process starts with the truck at the plant, as shown in block 101. The truck moves to the batch plant to be loaded, as indicted with the stages "Begin Load" 102 and "End Load" 103. The truck then moves to the slump/wash rack, as shown in block 104. At this stage, the truck is washed and the slump is adjusted if necessary by adding water. The truck then goes to the jobsite, is indicated by blocks for "Leave Plant" 105 and "Arrive Site" 106. The start and end of pouring are indicated with block for "Begin Pour" 107 and "End Pour" 108. After pouring, the driver may wash the truck of residual concrete, indicated with the "Washing" 109 stage. The truck then returns to the plant, as indicated in the blocks for "Leave Jobsite" 110 and "At Plant" 101. Washing should be performed as soon as practical after finish pour, but in some cases may need to take place after the truck has left the jobsite.

It is important to know at which stage or stages water is added. Water added to the drum from "Begin Loading" 102 to "Arrive Jobsite" 106 is used to adjust the concrete to within the mix design requirements and is the responsibility of the concrete supplier. Although it is typically the objective of the concrete supplier to reach the "Arrive Jobsite" 106 stage with the correct slump and water content, it is sometimes necessary for the supplier to add water between "Arrive Jobsite" 106 and "Begin Pour" 107 to adjust the concrete within design. The purchaser may decide to change the slump from what was originally ordered by adding water between "Arrive Jobsite" and "End Pour". This change could be outside the design parameters for the mix. Therefore, the concrete supplier should record the request and measure the amount of water added. Further, any water added between "Begin Pour" and "End Pour" could be applied to a partial load size and will have a greater effect when considering the basis of water per unit volume of concrete. If water is added to the drum between "End Pour" and "Begin Loading" on the next batch, but the drum is not emptied before "Begin Loading", then this water should be accounted for as being in the next batch.

Figure 7:
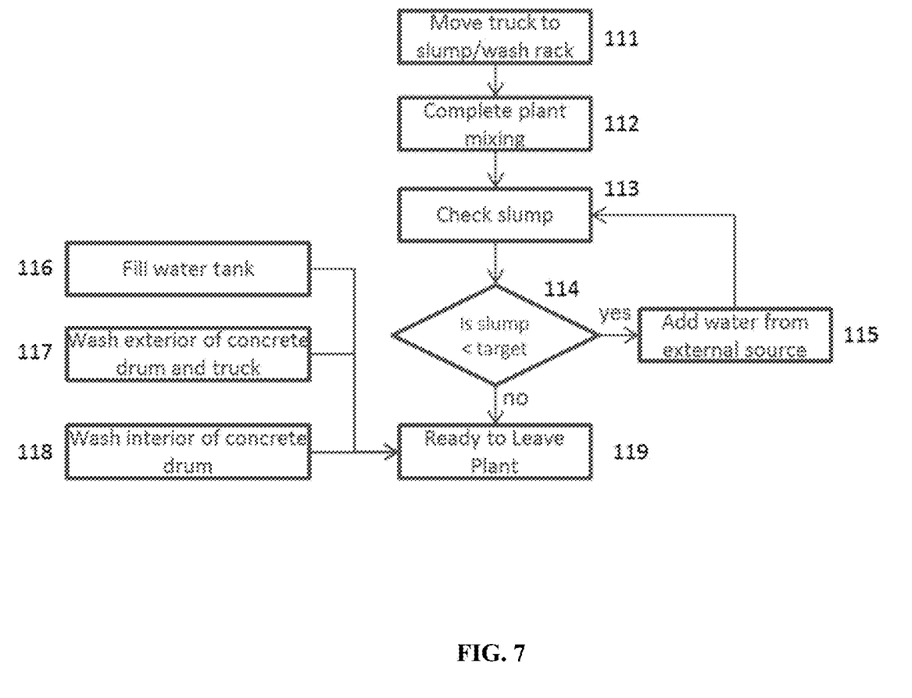
FIG. 7 is a flow chart of the sub-process for adding water at the slump/wash rack in accordance with an embodiment of the present disclosure.

The process at the slump/wash rack is further illustrated in the flow diagram in FIG. 7. The driver first moves the truck to the slump/wash rack, as shown in block 111. The driver operates the drum to complete mixing of the concrete in block 112. Specifications for concrete typically require a minimum number of revolutions of the concrete drum within a certain drum speed range to complete mixing. With mixing complete, the slump is checked in block 113. The slump can be checked by taking a sample of concrete from the drum and performing a slump test in accordance with industry standards such as ASTM C143. Alternatively, the slump can be estimated by visual observation of the concrete or by monitoring the amount of hydraulic pressure required to rotate the drum at a given drum speed. The slump is compared to a target value in block 114. If the slump is less than target, water is added to the drum from the external source as shown in block 115. The slump is again checked and adjusted until it is within target. Simultaneously to this process, the driver can fill the water tank on the drum, wash the exterior of the truck and drum, and wash the interior of the drum, as indicated in blocks 116, 117, and 118. Once all these steps are complete, the truck is ready to leave the plant as shown in 119.

The process illustrated in FIG. 7 is advantageous for numerous reasons, including, for example, because it allows water added to the drum to be recorded separately from water used for washing the exterior of the drum. It also enables blocks 116, 117, and 118 to be done in parallel with processes 111, 112, 113, 114, and 115, resulting in time savings in the plant. Contemporary systems made it necessary to wash the interior and exterior of the truck before adjusting slump, or run the risk of adding unknown volumes of water to the drum.

The embodiment illustrated in FIG. 2 and described above may be employed in this process. For example, the check valve 19 prevents water from flowing from the external source 25 to the truck tank 1. Therefore, the truck tank can remain unpressurized and be filled with water through tank port 2. At the same time, water can flow from the external source to the drum and be recorded by meter 14. In addition, any water to clean the inside of the drum can be added through hose 17 and nozzle 18, such that it is recorded by meter 14. In fact, water can be added to the drum via hose 7 and hose 17 simultaneously.

In prior art systems, water was added at the slump rack from an external source—both for washing the inside of the drum and adjusting slump—without passing through the meter 14. This was done so that it could be completed in parallel with washing the outside of the drum, filling the water tank, and completing mixing.

Alternatively, water could have been added at the slump rack from the truck tank and recorded by the graduated sight glass 6 or water meter 14; however, this water addition would need to have been done after filling the tank. It is also likely that the tank would again need to be refilled to ensure enough water available on the jobsite. The process would comprise filling the tank, adjust the slump and cleaning the inside of the drum, then refilling the tank. So, the process would assure water is measured but would be time consuming.

Data on the concrete properties is stored in concrete quality software. This software is used to store concrete mix designs. The software links to batch and dispatch software to send mix designs for use in production. Production data on the actual amounts batched is sent automatically from batch, dispatch, and truck tracking software. In addition, users can input test data on the concrete properties, such as results for slump, air content, setting time, and compressive strength. By adding data to the quality software on the total water added to the concrete, users can use the data in the quality software to track performance of production mixes, make adjustments to ensure quality and economy, and develop new mixture designs based on historical data. In contemporary concrete quality software, water added at the slump rack is not recorded, so the total water quantity stored in the software is not accurate.

Thus, an exemplary metering apparatus of the present disclosure for a concrete truck having a concrete drum and a water tank comprises: a coupling for connecting to an external water supply; a first check valve downstream of the coupling and upstream of a first joint, for preventing water from flowing toward the coupling; a second check valve downstream of the water tank and upstream of a first joint, for preventing water from flowing toward the water tank; and a meter downstream of the first joint and upstream of the concrete drum, for measuring water flow to the concrete drum from the external water supply and the water tank. The first check valve is open when water is added from the external water supply and closed when water is added from the truck water tank. The second check valve is open when water is added from the truck water tank and closed when water is added from the external water supply.

The exemplary metering apparatus may also have a first connection port, upstream of the meter, for a first hose and nozzle for spraying the exterior of the concrete truck. This first connection point can be a second joint downstream of the first joint and upstream of the meter. This location can be selected so that water not added to the concrete does not get recorded by the water meter. The exemplary metering apparatus can also have a second connection port, downstream of the meter, for a second hose and nozzle for spraying the interior of the concrete drum. This second connection port can be a third joint downstream of the meter and upstream of the concrete drum. This location may be selected so that water added to the concrete drum through the second hose and nozzle is recorded by the meter.

In a further exemplary embodiment of the present disclosure, the metering apparatus may also have both a first connection port, upstream of the meter, for a first hose and nozzle, and a second connection port, downstream of the meter, for a second hose and nozzle. The first connection point is a second joint downstream of the first joint and upstream of the meter. The second connection port is a third joint downstream of the meter and upstream of the concrete drum.

An exemplary system of the present disclosure for metering water on a concrete truck, the system may include a concrete truck comprising: a concrete drum, a water tank, and a metering device having a coupling for connecting to an external water supply; a first check valve downstream of the coupling and upstream of a first joint, for preventing water from flowing toward the coupling; a second check valve downstream of the water tank and upstream of a first joint, for preventing water from flowing toward the water tank; and a meter downstream of the first joint and upstream of the concrete drum, for measuring water flow to the concrete drum from the external water supply and the water tank; a concrete plant for loading materials into the concrete truck, and a jobsite where concrete is unloaded from the concrete drum. Some embodiments may further include a controller configured to record the meter readings at least one of prior to loading the concrete drum at the concrete plant, after loading the concrete drum at the plant, prior to arriving at a site destination, after arriving at the site destination prior to pouring concrete at the site destination, during pouring at the site destination, and after pouring concrete at the site destination. A truck tracking system may be included to determine these locations based on data from GPS, for instance, and other sensors mounted on the truck, such as drum rotation sensors.

A concrete truck may have a computer having a controller configured to receive data from a transmitting unit and to receive or calculate the total water added that can be added to the concrete drum. A concrete plant may include a computer-implemented batch control system comprising: a receiving unit for receiving data including quantities of ingredients loaded into the concrete drum, and a transmitting unit that is configured for transmitting at least a portion of the data to a controller. The amount of water that can be added without exceeding the design water content can be calculated by the batch software and sent to the computer onboard the truck, or can be calculated on board the truck. This amount of water that can be added without exceeding the design water content is calculated as the amount of water in the mix design, less any water added at batching including residual water left in the concrete drum from before loading, metered water added during batching, water in the form of moisture on the aggregates, and water contained in chemical admixtures. The amount of water available to add should be known to the driver, contractor, and inspector. The amount should not be exceeded without approval from an authorized individual. Typically, ready mix concrete companies require that a contractor sign a delivery ticket to authorize the addition of water in excess of design. By signing, the contractor normally accepts responsibility for the consequences of adding water in excess of design.

The exemplary system of the present disclosure may include a computer-implemented quality control system having, for example, a data storage unit configured to store data comprising the quantities of ingredients loaded into the concrete drum, the total water added to concrete in the drum, and concrete test data including at least one of slump, air content, and compressive strength, and a comparing unit configured to compare the amount of water added to the concrete test data. The addition of more water typically results in increased slump and reduced compressive strength. A quality control manager can use information provided by the devices, systems, and methods described herein, in a quality control system to ensure mixes are properly designed, among other useful and advantageous purposes. If a concrete mix in production consistently has more or less water than design, then the design can be adjusted. If compressive strength is too low, the amount of water added can be evaluated and adjusted in the design to ensure that future batches have adequate compressive strength.

An exemplary method of the present disclosure for metering water to a concrete truck having a concrete drum and a water tank, generally involves adding concrete to the concrete drum; adding water to a concrete drum from at least one of an external water supply and a water tank on the truck, the external water supply upstream of a first check valve, the first check valve upstream of a first joint, the water tank upstream of a second check valve, the second check valve upstream of the first joint; and measuring water added to the concrete drum from the external water supply and the water tank with a meter downstream of the first joint. In some embodiments, water added is measured prior to loading the concrete drum at a plant, after loading the concrete drum at the plant, prior to arriving at a site destination, after arriving at the site destination prior to pouring concrete at the site destination, during pouring concrete at the site destination, after pouring concrete at the site destination, or any combination thereof. The exemplary method may include reporting the amount of water added prior to loading the concrete drum at a plant, after loading the drum at the plant, prior to arrive at a site destination, after arriving at the site destination prior to pouring concrete at the site destination, during pouring concrete at the site destination, and after pouring concrete at the site destination, for example, or any combination thereof In some embodiments, the method includes comparing the water added to predetermined design criteria and issuing a warning signal if the water added exceeds a predetermined design criterion. The warning signal can be transmitted to a quality control manager, for example, to adjust the mix design so that future batches can be delivered at the correct slump without exceeding the design water content needed to achieve the required strength and durability. One of ordinary skill should appreciate that other advantageous uses of the warning signal, as well as of the data provided by the devices, systems, and methods described herein, are available.

EXAMPLE

Table 1 shows metered water data collected with a prototype metering apparatus as described herein for five deliveries from a concrete plant. An embodiment of the systems described herein was used in connection with the prototype to transmit the metered water data to a quality management system and allow an engineer to compare water added data with concrete property data on slump, air content, and compressive strength shown in the table.

In the first load, batched at 7:02 am, the mix design allowed 363 gal of water. Only 314.44 gal was added during batching, which left 48.56 gal to be added to the concrete after batching and until pouring. In this case, 6 gal was added at the plant and a further 27 gal was added after the truck arrived on site and before begin pour. After begin pour, an additional 2 gal was added. The total water added at end pour was 349.44 gal, which is less than the mix design allowance of 363 gal. Because less water was used than allowed by the mix design, the concrete was in conformance with design.

In the second load, batched at 7:10 am, a different mix design was used. In this case, the maximum water was 374 gal for an 11 yd$^3$ load. Again, less water was added during batching than allowed by design. Some water was added at the plant and again at the jobsite. The water added caused the amount of water to exceed design after begin pour. At this time, the contractor would have been responsible for the concrete and any consequence of excess water. The concrete was delivered to site within the design water content by the concrete supplier.

In the third load, batched at 8:45 am, the same mix design as the first load, batched at 7:02 am, was used. In this case, more water was added at batching, which meant that no water needed to be added at the plant. The batch plant operator can use the data indicating the first load had too little water after batching to add more water to the next load of the same mix design, thus eliminating the need to adjust the load in the plant and reducing the amount of time the truck spends in the plant from 15.9 to 8.5 minutes. The total water at arrive site and begin pour were similar. This is expected because both loads were the same mix design. Likewise, the slump, air content, and compressive strength were similar.

The fourth load, batched at 8:50 am, was batched with less water than design. However, the amount of water added at the plant caused the total water to exceed design. Additional water was added at the jobsite. This data indicates that the mix should be redesigned to ensure enough water is available to reach the design slump at begin pour.

The fifth load, batched at 9:17 am, was the same mix design as the fourth load. In this case, the load size was larger so more water could be added per the load. The total amount of water added by end pour was less than the 418 gal allowed by design. The less water required compared to the fourth load was likely due to the shorter time from batching to pouring. As concrete losses slump over time, more water is required. The lower water content compared to design was reflected in higher compressive strength at 28 days.

TABLE 1

Metered Water Data

| Date | Jan. 1, 2014 | Jan. 2, 2014 | Jan. 3, 2014 | Jan. 4, 2014 | Jan. 4, 2014 |
|---|---|---|---|---|---|
| Time | 7:02:57 AM | 7:10:00 AM | 8:45:05 AM | 8:50:58 AM | 9:17:43 AM |
| Ticket ID | 86216 | 86217 | 86218 | 86219 | 86229 |
| Truck ID | 1386 | 1440 | 1614 | 1442 | 1617 |
| Mix ID | TSD05R11 | TAJ05R13 | TSD05R11 | TAGB8P30 | TAGB8P30 |
| Load Size, yd$^3$ | 11.0 | 11.0 | 11.0 | 10.0 | 11.0 |
| Mix Design Water, gal | 363 | 374 | 363 | 380 | 418 |
| Water During Batching, gal | 314.44 | 330.10 | 340.27 | 359.42 | 397.07 |
| Water Added (Begin Load to Leave Plant), gal | 6.00 | 5.00 | 0.00 | 60.00 | 0.00 |
| Water Added (Leave Plant to Arrive Site), gal | 0.00 | 0.00 | 0.00 | 0.00 | 0.00 |
| Water Added (Arrive Site to Begin Pour) gal | 27.00 | 21.00 | 0.00 | 21.00 | 10.00 |
| Water Added (Begin Pour to End Pour), gal | 2.00 | 34.00 | 1.00 | 25.00 | 6.00 |
| Total Water Added at Leave Plant, gal | 320.44 | 335.10 | 340.27 | 419.42 | 397.07 |
| Total Water Added at Arrive Site, gal | 320.44 | 335.10 | 340.27 | 419.42 | 397.07 |
| Total Water Added at Begin Pour, gal | 347.44 | 356.10 | 340.27 | 440.42 | 407.07 |
| Total Water Added at End Pour, gal | 349.44 | 390.10 | 341.27 | 465.42 | 413.07 |
| Leave Plant, min | 15.9 | 11.7 | 8.5 | 14.0 | 9.2 |
| Arrive Site, min | 29.5 | 28.6 | 21.4 | 35.7 | 28.5 |
| Begin Pour, min | 42.7 | 36.7 | 30.3 | 72.7 | 41.0 |
| End Pour, min | 71.2 | 71.2 | 68.8 | 139.5 | 87.7 |
| Air Content (at site), % | 3.2 | 3.4 | 3.0 | 2.8 | 3.9 |
| Slump (at site), inches | 5 | 6 | 4.5 | 5.25 | 5.5 |
| Compressive Strength (28-day), psi | 4256 | 3478 | 4280 | 5607 | 6210 |

The terminology used herein is for the purpose of describing particular embodiments only and is not intended to be limiting of the approach. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The apparatus, systems, and methods described herein may be embodied in other specific forms without departing from the spirit or essential characteristics thereof. The present embodiments are therefore to be considered in all respects as illustrative and not restrictive, the scope of the disclosure being indicated by the claims of the application rather than by the foregoing description, and all changes which come within the meaning and range of equivalency of the claims are therefore intended to be embraced therein.

What is claimed is:

1. A metering apparatus for a concrete truck having a concrete drum, the apparatus comprising:
   (a) a water tank;
   (b) an external water supply;
   (c) a coupling connected to the external water supply;
   (d) a first check valve downstream of the coupling and upstream of a first joint preventing water from flowing toward the coupling and the external water supply;
   (e) a second check valve downstream of the water tank and upstream of the first joint preventing water from flowing toward the water tank;
   (f) a meter downstream of the first joint and upstream of the concrete drum measuring water flow to the concrete drum from the external water supply and the water tank;
   (g) a first connection port downstream of the first joint and upstream of the meter connected to a first hose and the first hose connected to a first nozzle for spraying the exterior of the concrete truck with water; and
   (h) a second connection port downstream of the meter connected to a second hose and the second hose connected to a second nozzle for spraying the interior of the concrete drum with water,
   wherein the meter records the amount of water used from the second hose and the second nozzle to wash the interior of the concrete drum but does not record the amount of water used from the first hose and the first nozzle to wash the exterior of the concrete truck.

2. A system for metering water on a concrete truck, the system comprising:
   a concrete truck comprising:
   (a) a concrete drum;
   (b) a water tank; and
   (c) a metering device having:
      i. a coupling connected to an external water supply;
      ii. a first check valve downstream of the coupling and upstream of a first joint preventing water from flowing toward the coupling and the external water supply;

iii. a second check valve downstream of the water tank and upstream of the first joint preventing water from flowing toward the water tank;

iv. a meter downstream of the first joint and upstream of the concrete drum measuring water flow to the concrete drum from the external water supply and the water tank;

v. a second joint downstream of the first joint and the external water source and upstream of the meter connected to a first hose and nozzle for spraying the exterior of the concrete truck with water;

vi. a third joint downstream of the meter and upstream of the concrete drum connected to a second hose and nozzle for spraying the interior of the concrete drum with water;

vii. a first ball valve downstream of the first joint and upstream of the second joint for controlling water flowing to the concrete drum, the first hose and nozzle, and the second hose and nozzle; and viii. a second ball valve downstream of the third joint and upstream of a third hose and nozzle for controlling water flowing to the concrete drum and the third hose and nozzle, and a concrete plant.

3. The system of claim 2, further comprising a controller configured to record meter readings at least one of prior to loading the concrete drum at the concrete plant, after loading the concrete drum at the plant, prior to arriving at a site destination, after arriving at the site destination prior to pouring concrete at the site destination, during pouring at the site destination, and after pouring concrete at the site destination.

4. The system of claim 2, wherein the truck further comprises a computer having a controller configured to receive data from a transmitting unit and to receive data indicative of the total water that can be added to the concrete drum, and the concrete plant includes a computer-implemented batch control system comprising:

a receiving unit for receiving data including quantities of ingredients loaded into the concrete drum, and a transmitting unit that is configured to transmit at least a portion of the data indicative of the total water that can be added to the concrete drum to the controller.

5. The system of claim 4, further comprising a computer-implemented quality control system comprising:

a data storage unit configured to store data comprising the quantities of ingredients loaded into the drum, the total water added to the drum, and concrete test data including at least one of slump, air content, and compressive strength, and a comparing unit configured to compare the amount of water added to the concrete test data.

6. The system of claim 5, wherein the comparing unit is configured to compare the water flow to the concrete drum to a predetermined design criteria.

7. The metering apparatus of claim 1, wherein the first connection port is downstream of the water tank and the external water source.

8. The metering apparatus of claim 1, wherein the second connection port is connected to a third hose and the third hose is connected to a third nozzle for adding water to the concrete drum, whereby the meter records the amount of water used from the third hose and third nozzle.

9. The metering apparatus of claim 8 further including a first ball valve downstream of the first joint and upstream of the first connection port for controlling water flowing to the concrete drum, the first hose and the first nozzle, the second hose and the second nozzle, and the third hose and the third nozzle.

10. The metering apparatus of claim 9 further including a second ball valve downstream of the second connection port and upstream of the third hose and the third nozzle for controlling water flowing to the concrete drum and the third hose and the third nozzle.

11. A metering apparatus for a concrete truck having a concrete drum, the apparatus comprising:

(a) a water tank;

(b) an external water supply;

(c) a coupling connected to the external water supply;

(d) a first check valve downstream of the coupling and upstream of a first joint preventing water from flowing toward the coupling and the external water supply;

(e) a second check valve downstream of the water tank and upstream of the first joint preventing water from flowing toward the water tank;

(f) a meter downstream of the first joint and upstream of the concrete drum measuring water flow to the concrete drum from the external water supply and the water tank;

(g) a first connection port downstream of the first joint and upstream of the meter directly connected to a first hose and the first hose directly connected to a first nozzle for spraying the exterior of the concrete truck with water; and (h) a second connection port downstream of the meter directly connected to a second hose and the second hose directly connected to a second nozzle for spraying the interior of the concrete drum with water, wherein the meter records the amount of water used from the second hose and the second nozzle to wash the interior of the concrete drum but does not record the amount of water used from the first hose and the first nozzle to wash the exterior of the concrete truck.

12. The metering apparatus of claim 11, wherein the second connection port is directly connected to a third hose and the third hose is directly connected to a third nozzle for adding water to the concrete drum, whereby the meter records the amount of water used from the third hose and the third nozzle.

* * * * *